United States Patent [19]

Szantay et al.

[11] 4,399,069

[45] Aug. 16, 1983

[54] PROCESS FOR AN ENANTIOSELECTIVE SYNTHESIS OF OPTICALLY ACTIVE 14-OXO-E-HOMO-EBURNANE DERIVATIVES

[75] Inventors: Csaba Szantay; Lájoś Szabo; György Kalaus; Janos Sapi; János Kreidl; Mária Fàrkas née Kirjak; Andras Nemes; Laszlo Cibula, all of Budapest, Hungary

[73] Assignee: Richter Gedeon Vegyeszeti Gyar Rt., Budapest, Hungary

[21] Appl. No.: 312,128

[22] Filed: Oct. 16, 1981

[30] Foreign Application Priority Data

Oct. 12, 1980 [HU] Hungary ............................ 2525

[51] Int. Cl.³ .................. C07D 471/14; C07D 471/22
[52] U.S. Cl. ................................. 260/239.3 P; 546/70
[58] Field of Search .................... 260/239.3 P; 546/70

[56] References Cited

U.S. PATENT DOCUMENTS 3,770,724  11/1973  Warnant et al. ............ 260/239.3 P
4,283,401   8/1981  Szantay et al. ...................... 546/70

FOREIGN PATENT DOCUMENTS 2010833A  7/1979  United Kingdom ........ 260/239.3 P
1548671   7/1979  United Kingdom ................ 546/70
2028809A  3/1980  United Kingdom ................ 546/70
2051794A  1/1981  United Kingdom ................ 546/70

OTHER PUBLICATIONS

Synthesis of Vinca Alkaloids and Related Compounds, IX, L. Szabo, Gy. Kalaus, K. Nogradi, Cs. Szantay, Acta Chimica Acad. Sci. Hung., 99(1), 73–89 (1979).

Primary Examiner—Robert T. Bond
Attorney, Agent, or Firm—Karl F. Ross; Herbert Dubno

[57] ABSTRACT

The invention relates to a new enantioselective synthesis for the preparation of optically active 14-oxo-E-homo-eburnane derivatives of the formula (Ia)

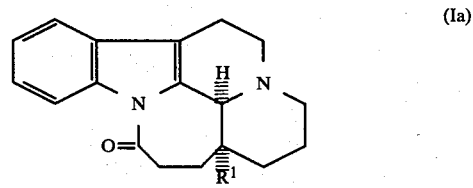

wherein $R^1$ is alkyl having from 1 to 4 carbon atom.

In the synthesis optically active 6-alkoxycarbonylhexahydroindoloquinolizinium salts are employed as starting materials, which contain a center of chirality at the site of attachment of the carboxyl group. This center of chirality preserves the optical activity of the optically active tryptophan ester from which this compound has been prepared until a new center of chirality is formed in the molecule in a configuration corresponding to the desired end product. The carboxyl group, which is not needed in the end product and only serves to preserving the optical activity can then be eliminated.

Compounds of the formula (Ia) are known in the art and may be used in the synthesis of (+)-vincamine and (+)-apovincaminic acid ethylester.

25 Claims, No Drawings

PROCESS FOR AN ENANTIOSELECTIVE SYNTHESIS OF OPTICALLY ACTIVE 14-OXO-E-HOMO-EBURNANE DERIVATIVES

The invention relates to a new process for an enantioselective synthesis of optically active 14-oxo-E-homo-eburnane derivatives of the formula (Ia)

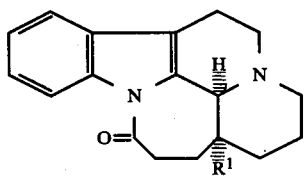

wherein $R^1$ is alkyl having from 1 to 4 carbon atoms.

According to the invention compounds of the formula (Ia), in which $R^1$ is as defined above, are prepared by reacting an optically active 6-alkoxy-carbonyl-hexahydroindoloquinolizinium salt of the formula (II)

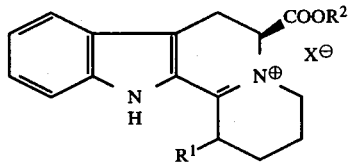

wherein
$R^1$ has the same meaning as defined above,
$R^2$ is alkyl having from 1 to 4 carbon atoms and
X represents a residue of an acid, with a methylenemalonic acid diester derivative of the formula (III)

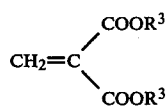

wherein $R^3$ is alkyl having from 1 to 4 carbon atoms, in the presence of a basic catalyst, subjecting a new, optically active 6-alkoxycarbonyl-hexahydroindoloquinolizinium-1-yl-methylene malonate salt of the formula (IV)

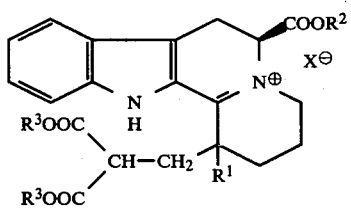

wherein $R^1$, $R^2$, $R^3$ and X have the meanings defined above, to an acid hydrolysis followed by an alkaline hydrolysis, subjecting a new, optically active hexahydroindoloquinoliziniumcarboxylic acid derivative of the formula (V)

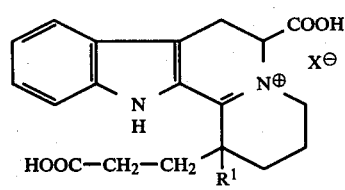

obtained, wherein $R^1$ and X have the meanings defined above, to selective decarboxylation, saturating a new, optically active hexahydroindoloquinoliziummonocarboxylic acid of the formula (VI)

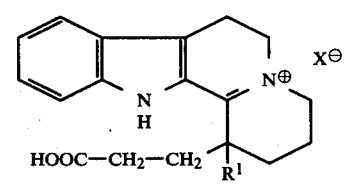

obtained, wherein $R^1$ and X are as defined above, and cyclizing an optically active octahydroindoloquinolizinemonocarboxylic acid derivative of the formula (VII)

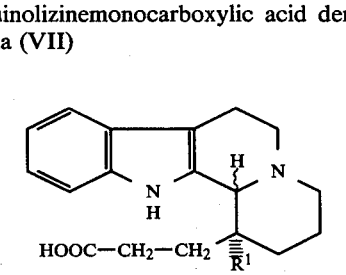

obtained, wherein $R^1$ is as defined above, optionally without isolation, or subjecting the same compound after isolation to esterification, or subjecting first a compound of the formula (VI), wherein $R^1$ and X are as defined above, to esterification and saturating the compound obtained to give a corresponding optically active octahydroindoloquinolizine ester derivative of the formula (VIII)

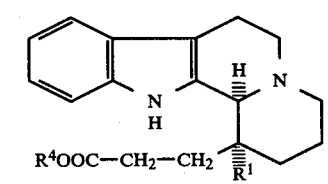

wherein $R^1$ has the meanings defined above and $R^4$ stands for an alkyl group having from 1 to 4 carbon atoms, and finally cyclizing the compound obtained in a manner known per se.

In the compounds of the formulae (Ia), (II), (III), (IV), (V), (VI), (VII) and (VIII) $R^1$, $R^2$, $R^3$ and $R^4$ represent an alkyl having from 1 to 4 carbon atoms, more particularly, a straight or branched chain alkyl group having from 1 to 4 carbon atoms, e.g. methyl, ethyl, n-propyl-, isopropyl, n-butyl, sec-butyl and tert-butyl.

The intermediates of the formula (IV), (V), and (VI) are new compounds.

The optically active compounds of the formula (Ia) are known in the art and may be used in the synthesis of (+)-vincamine and (+)-apovincaminic acid ethylester (Cavinton$^R$), which have cerebral vasodilating activity.

There are numerous processes known in the art for the preparation of (+)-vincamine and (+)-apovincaminic acid ethylester (see e.g. JACS, 1540 (1979). In most of them one of the racemic intermediates is resolved and the desired antipode obtained is subjected to the subsequent synthesis steps. This corresponds to a loss of at least 50%. It is therefore desirable to provide an enantioselective synthesis for the production of (+)-vincamine and/or (+)-apovincaminic acid ethylester. The present invention relates to such a synthesis which ensures that an optically active starting material having a desired configuration preserves its optical activity as long as it is desired.

Similar efforts have already been made for an asymmetric synthesis of (+)-vincamine (Acta Chim. Hung. 99, 73 (1979)). In the process reported in the cited article the naturally occuring L-tryptophan was employed as a starting material. The starting compound was first converted into its isopropyl ester whereupon the obtained L-tryptophan isopropylester was reacted with an ethylvaleric acid chloride derivative, the chloropentanoyltryptophan isopropylester was subjected to ring closure by means of phosphorus oxychloride in benzene and was then treated with a mild base in methylene chloride to yield the perchlorate of optically active 1-ethyl-hexahydroindoloquinolizine-6-carboxylic acid isopropylester of the formula (II). Before the subsequent step of electrophilic alkylation with an acrylic acid ester derivative, however, from the perchlorate the corresponding base had to be liberated. This treatment was carried out in methylene chloride, with a 2% aqueous sodium hydroxide solution. The product obtained after this treatment proved to be racemic. Accordingly, the conclusion can be drawn that in a higher pH range the optical activity of the carbon atom next to the ester group is lost, while at a lower pH-value the base cannot be set free from its perchlorate. While the electrophilic alkylation on the 1-carbon atom of the indolo(2,3-a)quinolizine skeleton can be performed only if the free base is used, the liberation of the free base from the corresponding indoloquinolizinium salt is unavoidable.

We have surprisingly found that a chiral indolo(2,3-a)quinolizinium salt may be alkylated in the presence of a catalytic amount of strong bases, preferably alkali metal alcoholates, such as potassium tert.-butylate, without attacking the chirality center. Up to the present, the use of a catalytic amount of strong bases during alkylation has been reported only in connection with non-chiral compounds (Tetrahedron 34, 3001–3004 (1978) and Hungarian Patent Application No. RI-713). By this alkylation method the addition reaction could be completed when reacting a hexahydroindoloquinolizinium salt and a corresponding, reactive olefin, such as acrolein or methylenemalonic acid ester.

As starting materials of the process according to the invention the intermediates described in the Hungarian Patent Application 781/80 are used. These compounds are characterized by the formula (II) and have a considerable optical rotatory power.

In a process disclosed in the Hungarian Patent Application No. 781/80 it was attempted to produce the E ring of eburnane skeleton from a chiral starting material, using the highly reactive acrolein as an electrophilic alkylating agent. By this method, however, the product could be obtained in an optical purity of about 62% only.

The optically active starting compounds of the formula (II) can be prepared by reacting an optically active tryptophan ester derivative with an alkylvaleric acid halide in the presence of an acid binding agent and subjecting the optically active halopentanoyltryptophan ester derivative obtained to simultaneous cyclization and dehydration followed by a treatment with a base.

The optically active starting compounds of the formula (II) contain a center of chirality at the site of attachment of the carboxyl group. This center of chirality preserves the optical activity of the optically active tryptophan ester from which this compound has been prepared until a new center of chirality is constructed in the molecule in a configuration corresponding to the desired end product. After this the carboxyl group which is not needed in the end product and only served for preserving the optical activity can be eliminated any time. Although when the carboxyl group is eliminated, the center of chirality at the carbon atom to which it has been attached ceases to exist, the molecule already has the desired optical activity.

In the process according to the invention the reaction of the starting compounds of the formula (II) with the methylenemalonic acid diester derivatives of the formula (III) (which are even more reactive than acrolein) can be completed in an unusually short time, i.e. in about half to one hour and consequently, the end product is obtained in an optical purity exceeding 90%. This means that during the addition practically no racemization takes place or, in other words, the reaction velocity of the addition of methylenemalonic acid ester was much higher than the velocity of racemization. Optical purity was determined in comparision with the compounds of the formula (Ia) and (VIII), which have a known absolute optical rotation.

The preparation of the methylenemalonic acid esters of the formula (III) is described in J. Org. Chem. 4, 493 (1939).

Compounds of the formula (II) are reacted with compounds of the formula (III) in an inert organic solvent, under water-free conditions. As a solvent for example aliphatic or aromatic hydrocarbons optionally substituted by one or more halogens, e.g. dichloromethane, dichloroethane, chloroform, chlorobenzene can be employed. The reaction is performed in the presence of a catalytic amount of an alkali metal tertiary alcoholate, preferably potassium tert.-butylate, at a temperature of 0° to 35° C., preferably 10° to 25° C. Preferably freshly prepared compounds of the formula (III) are employed in a molar excess of about 1.1 to 2, preferably 1.1 to 1.4 related to the compounds of the formula (II). The alkali metal tertiary alcoholates are generally used in an amount of 3 to 7 molar %, preferably 4 to 6 molar % related to the compounds of the formula (II). The reaction is completed in about half to one hour, with a nearly quantitative yield. The new compounds of the formula (IV) are obtained as an oil, which can be characterized by its optical rotatory power.

The acid hydrolysis of the compounds of the formula (IV) is accomplished with a dilute aqueous mineral acid, preferably with a mineral acid easy to eliminate when evaporating the reaction mixture, e.g. a dilute aqueous hydrochloric acid solution. The acid hydrolysis is performed at an elevated temperature, preferably about the boiling temperature of the reaction mixture (80° to 120°

C.). The alkaline hydrolysis is preferably carried out with an aqueous solution of an alkali metal hydroxide, preferably sodium hydroxide. As a co-solvent alkanols having one to 4 carbon atoms, preferably ethanol, can be employed. After eliminating the alkanols, the alkali metal salts obtained during the neutralization following the hydrolysis are readily dissolved in the aqueous solution and accordingly do not contaminate the new, optically active compounds of the formula (V) obtained. Alkaline hydrolysis is preferably performed at room temperature (10° to 35° C.).

The selective decarboxylation of the compounds of the formula (V) is carried out thermally, at a temperature between 150° C. and 200° C., preferably 165° C. and 175° C., preferably in an inert organic solvent having a high boiling point. As a solvent any inert organic solvents having a boiling point between 150° C. and 200° C. may be employed, including decalin, tetralin, quinoline, isoquinoline, most preferably decalin.

The compounds of the formula (VI) are saturated with catalytically activated hydrogen or a chemical reducing agent. When the saturation is performed with catalytically activated hydrogen, metals, e.g. palladium, platinum, nickel, iron, copper, cobalt, chromium, zinc, molybdenum, tungsten and their oxides may be employed as a hydrogenating catalyst. Catalytic hydrogenation may be carried out also in the presence of catalysts which have previously been precipitated on the surface of a carrier. Such carriers include carbon, preferably charcoal, silica, alumina and sulfates and carbonates of alkali earth metals. Catalytic hydrogenation is accomplished in an inert solvent, e.g. water, aqueous alkaline solution, alcohols, ethyl acetate, dioxane, glacial acetic acid, dimethyl acetamide, dimethyl formamide or mixtures thereof. As a chemical reducing agent for example complex metal hydrides, e.g. borohydrides, such as alkali metal borohydrides, preferably sodium borohydride or aluminum hydrides such as lithiumaluminum hydride can be employed. Chemical reduction is performed in an inert solvent, e.g. water, aqueous alcohol, acetonitrile. Preferred solvents or suspending agents include aliphatic alcohols, e.g. methanol.

Following the process according to the invention compounds of the formula (VI) are most preferably saturated by catalytic hydrogenation in the presence of a palladium-on-charcoal catalyst, in an inert organic solvent, such as dimethyl formamide. As a result of catalytic hydrogenation an epimeric mixture of compounds of the formula (VII) is obtained, containing the cis isomer in an overwhelming majority. When hydrogenation is accomplished in the presence of a palladium-on-charcoal catalyst, in dimethyl formamide, C/D cis annelated 1α-alkyl-12αH-octahydro-indoloquinolizines are obtained stereoselectively and the corresponding trans 12bβH-epimers are obtained only as bis-products. If desired, the two epimers of the formula (VII) can be separated, but their separation is not required for the subsequent step.

Cyclization of the compounds of the formula (VII) is carried out with a phosphorus halide, phosphorus oxyhalide or sulfur oxyhalide, such as phosphorus pentachloride, phosphorus pentabromide, thionyl chloride, etc., preferably phosphorus oxychloride. The reaction temperature may be varied between 10° C. and 100° C., preferably between 15° C. and 30° C. The cyclization may also be performed at a temperature of 60° to 80° C. for one to 3 hours. As a result, compounds of the formula (Ia) are obtained with a good yield, in an optical purity of about 98%.

The process according to the invention is preferably carried out by subjecting the cis-trans mixture of the compounds of the formula (VII), obtained by saturating compounds of the formula (VI) to cyclization without isolation from the reaction mixture, thereby reducing the reaction steps of the synthesis according to the invention. When using this preferred embodiment, the total yield calculated for the starting compounds of the formula (II) amounts to about 35%. The optical purity of the compounds of the formula (Ia) obtained is about 96%. As a main product of the cyclization, compounds of the formula (Ia) are obtained but as a by-product several percent of a cis-trans isomeric mixture of the formula (Ib)

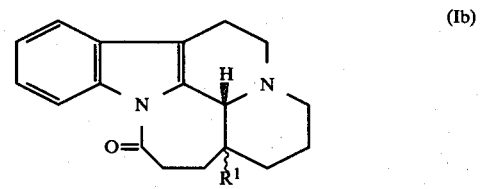

may also be isolated from the mother liquor.

According to another embodiment of the process according to the invention acids of the formula (VI) are first converted into the corresponding esters which are then saturated, or alternatively, they are saturated and then the acids of the formula (VII) obtained are converted into the corresponding esters. By both alternatives octahydroindoloquinolizine ester derivatives of the formula (VIII) are obtained, which are then cyclized in a known manner, for example by means of sodium ter.-butylate (Hungarian Patent Specification No. 163,769). The esterification of the compounds of the formula (VI) and (VII), respectively is carried out as described in the British Patent Specification No. 1,548,671 for the esterification of certain compounds of the formula (VII). When the methyl esters are to be prepared, the corresponding acids are preferably reacted with diazomethane in an inert organic solvent, such as halogenated hydrocarbons, preferably dichloromethane.

Compounds of the formula (Ia) prepared according to the invention if desired, may be subjected to further purification, e.g. recrystallization.

The new enantioselective synthesis for the preparation of the compounds of the formula (Ia), which are useful intermediates in the preparation of pharmaceutically active alkaloids having an eburnane skeleton, provides the desired products with a very good yield, in a high optical purity. The reactions involved are very easy to carry out. A further advantage of the process according to the invention consists in the fact that by using extremely reactive compounds of the formula (III), to an extent which renders the racemization practically impossible. In the second step of the synthesis by acid and a subsequent alkaline hydrolysis of the compounds of the formula (IV) dicarboxylic acids of the formula (V) can be prepared, from which the functional carboxyl group preserving the original chirality can be eliminated by selective decarboxylation, without any difficulty. After stereoselective saturation of the C=N bond of the new carboxylic acids of the formula (VI) the compounds obtained can directly be transformed into the desired compounds of the formula (Ia), and the conversion can be performed with an excellent yield, giving the compounds of the formula (Ia) in a high optical purity.

Further details of the invention are illustrated by the following Examples, which are not intended to limit the scope of invention.

EXAMPLE 1

(−)-1α-Ethyl-1β-(2′,2′-diethoxycarbonylethyl)-6β-methoxycarbonyl-1,2,3,4,6,7-hexahydro-12H-indolo(2,3-a)quinolizin-5-ium perchlorate 2.00 g. (4.87 mmoles) of (+)-1-ethyl-6β-methoxycarbonyl-1,2,3,4,6,7-hexahydro-12H-indolo(2,3-a)quinolizin-5-ium perchlorate ($[\alpha]_{546}^{22} = +135°$, c=1, dichloromethane) are dissolved in 15 ml. of absolute dichloromethane whereupon 1.10 ml. (1.16 g., 6.75 mmoles) of freshly prepared methylenemalonic acid diethylester (J. Org. Chem. 4, 493 (1939) are added to the solution, with stirring. To the reaction mixture cooled to 0° C. a suspension of 30 mg. (0.268 mmoles) of potassium tert.-butylate in 5 ml. of dichloromethane is added under stirring. At room temperature the reaction is completed within one hour. After neutralization with one drop of hydrochloric acid in ethanol, the solvent is eliminated from the reaction mixture in vacuo, whereupon the residue is triturated with two 8-ml. portions of ether, the ether is decanted and the oily product is released from ether in vacuo. 2.75 g. of the named compound are obtained as an oily product. Yield 96.5%

$[\alpha]_D^{23} = -10°$; $[\alpha]_{546}^{23} = -17°$ (c=1, dichloromethane).

IR spectrum (KBr): 3400 (indole NH), 1745, 1730 (ester CO groups) cm$^{-1}$.

EXAMPLE 2

(+)-1α-Ethyl-1β-carboxyethyl-6-carboxy-1,2,3,4,6,7-hexahydro-12H-indolo(2,3-a)quinolizin-5-ium perchlorate 1.50 g. (2.57 mmoles) of (−)-1α-ethyl-1β-(2′-diethoxycarbonylethyl)-6β-methoxycarbonyl-1,2,3,4,6,7-hexahydro-12H-indolo(2,3-a)quinolizin-5-ium perchlorate prepared in Example 1 are dissolved in 10 ml. of ethanol. To the solution 15 ml. of a 10% aqueous hydrochloric acid solution are added and the mixture obtained is refluxed for 24 hours.

From the reaction mixture the solvent is eliminated in vacuo, the residue is triturated with 5 ml. of ether whereupon ether is eliminated in vacuo.

The oily residue is dissolved in 30 ml. of ethanol and to the solution a solution of 0.62 g. (15.45 mmoles) of sodium hydroxide in 3 ml. of water is added. At room temperature the reaction terminates in 6 hours.

From the reaction mixture the solvent is eliminated in vacuo. The oily residue is dissolved in 7 ml. of water and the pH of the solution is adjusted to 3 with a 70% perchloric acid solution, under cooling with ice water. The yellow precipitate is filtered off, washed with 2 ml. of water and dried. 1.10 g. of the named compound are obtained, melting at 183° C. (decomp.).

Yield: 92.0%

$[\alpha]_D^{23} = +36°$; $[\alpha]_{546}^{23} = +47.5°$ (c=0.8, methanol).

IR spectrum (KBr): 3450-3300 (OH, indole-NH), 1715, 1620 (carboxylate), 1610 (C=N) cm$^{-1}$.

EXAMPLE 3

(−)-1α-Ethyl-1β-carboxyethyl-1,2,3,4,6,7-hexahydro-12H-indolo(2,3-a)quinolizin-5-ium perchlorate 1000 mg. (2.13 mmoles) of (+)-1α-ethyl-1β-carboxyethyl-6-carboxy-1,2,3,4,6,7-hexahydro-12H-indolo(2,3-a)-quinolizin-5-ium perchlorate in 15 ml. of decalin are heated at 160° to 170° C. for 25 minutes, with stirring. The substance melts accompanied by gas evolution. After cooling the reaction mixture is filtered, the solid obtained is washed decalin-free with three 5-ml. portions of ether and is dried. 880 mg. of the title compound are obtained. Yield: 97.2% $[\alpha]_D^{25} = -19°$.

IR spectrum (KRr): 3350 (indole NH), 1710, 1620 (carboxylate), 1580, 1520 (C=N) cm$^{-1}$.

EXAMPLE 4

(−)-1α-Ethyl-1β-methoxycarbonylethyl-1,2,3,4,6,7-12,12b -octahydro-indolo(2,3-a)quinolizine 660 mg. (1.55 mmoles) of (−)-1α-ethyl-1β-carboxyethyl-1,2,3,4,6,7-hexahydro-12H-indolo(2,3-a)quinolizin-5-ium perchlorate prepared in Example 3 are dissolved in 10 ml. of absolute dimethyl formamide and subsequently hydrogenated in the presence of 800 mg. of a prehydrogenated 10% palladium-on-charcoal catalyst.

When the calculated amount of hydrogen has been taken up, the catalyst is filtered off, washed with two 5-ml. portions of dimethyl formamide and the combined organic phases are evaporated to dryness under a pressure of 1 to 2 mm Hg.

The oily residue is dissolved in a mixture of 15 ml. of dichloromethane and 5 ml. of methanol and a solution of an excess amount of diazomethane in dichloromethane is added under outer ice cooling, with stirring (A. Vogel: Practical Organic Chemistry 3rd Edition, p. 971). The progress of the reaction is monitored by thin layer chromatography (KG-G, a 14:3 mixture of benzene and methanol).

From the reaction mixture the solvent is eliminated in vacuo, the residue is dissolved in 20 ml. of dichloromethane and the base is liberated by shaking the solution with 5 ml. ov a 10% aqueous sodium carbonate solution. After a further extraction with 5 ml. of dichloromethane the organic phases are separated, combined, dried on anhydrous magnesium sulfate, filtered and from the filtrate the solvent is eliminated in vacuo.

610 mg. of an oily product are obtained containing the title compound as a main component.

The mixture is separated into three components by preparative thin layer chromatography (KG-PF$_{254+366}$, a 140:30 mixture of benzene and methanol, elution:acetone). The substance having the lowest R$_f$ value weights 240 mg. Yield: 45.5% of the named compound.

For the crude product $[\alpha]_D^{21} = -92°$, $[\alpha]_{546}^{21} = -110°$.

(c=2.14, dichloromethane).

240 mg. of the oily product are dissolved in 0.5 ml. of methanol and the pH of the solution is adjusted to 6 with hydrochloric acid in methanol. The precipitated crystals are filtered off and dried. 180 mg. of the named compound were obtained as a hydrochloric acid salt. Yield: 40.0%.

$[\alpha]_D^{22} = -118°$; $[\alpha]_{546}^{22} = -143°$ (c=1.38, dichloromethane).

The optical rotatory powers correspond to the base set free from the hydrochloride.

The maximum value measured up to now is $[\alpha]_D^{25} = -121°$ (c=2.02, dichloromethane, Hungarian Patent Application No. RI-633).

IR spectrum (KBr): 3400 (indole NH), 1735 (ester CO) cm$^{-1}$.

The $^1$H-NMR and MS spectra of the compound are identical with the corresponding spectra of the compound prepared according to the Hungarian Patent Application No. RI-633.

As a by-product 50 mg. (10.5%) of (+)-14-oxo-E-homo-eburnane are obtained as an oily product which can be easily isolated.

Of the component having the highest $R_f$-value 35 mg. 7.3% could be isolated as an oily product which was identified as (+)-14-oxo-3-epi-E-homoeburnane.

$[\alpha]_D^{24} = +61°$ (c=1, dichloromethane).

The $R_f$-values decrease in the following order: (+)-14-oxo-3-epi-E-homo-eburane > (+)-14-oxo-E-homo-eburane > (−)-1α-ethyl-1β-methoxycarbonylethyl-1,2,3,4,6,7,12,12α-octahydro-indolo(2,3-a)quinolizine (KG-G, a 14:3 misture of benzene and methanol).

EXAMPLE 5

(+)-14-Oxo-E-homo-eburnane(3α,17α)

400 mg. (0.943 mmoles) of (−)-1α-ethyl-1β-carboxyethyl-1,2,3,4,6,7-hexahydro-12H-indolo(2,3-a)quinolizin-5-ium perchlorate prepared in Example 3 are dissolved in 9 ml. of absolute dimethyl formamide and hydrogenated in the presence of 800 mg. of a prehydrogenated 10% palladium-on-charcoal catalyst.

When the calculated amount of hydrogen is taken up, the catalyst is filtered off from the reaction mixture. The catalyst is then washed with two 5-ml. portions of dimethyl formamide and the combined organic phases are evaporated to dryness on a bath of 50° to 60° C., under a pressure of 1 to 2 mm Hg.

The oily residue is dissolved in 3 ml. of phosphorus oxychloride under cooling with ice and the solution is kept at room temperature for two or three days.

5 ml. of benzene are added to the reaction mixture and the unreacted phosphorus oxychloride is eliminated by distillation in vacuo. To the residue 5 ml. of water are added under cooling with ice, whereupon the pH is adjusted to 9 with a concentrated aqueous ammonium hydroxide solution. The organic precipitate is extracted with three 8-ml. portions of dichloromethane. The combined organic phases are dried on anhydrous magnesium sulfate, filtered and from the filtrate the solvent is distilled off in vacuo.

As a distillation residue 420 mg. of an oily product are obtained, which are then subjected to preparative thin layer chromatography (KG-PF $_{254+366}$, a 140:30 mixture of benzene and methanol, elution:acetone).

The substance having a lower $R_f$-value is the named compound, weighing 129 mg. (oily).

Yield: 44.4%.

$[\alpha]_D^{24} = +13°$, $[\alpha]_{546}^{24} = +19°$ (c=2, dichloromethane).

100 mg. of the oily product are crystallized from 0.5 ml. of methanol to yield 117 mg. (40%) of the named compound in a crystalline form.

$[\alpha]_D^{24} = +12°$, $[\alpha]_{546}^{24} = +18°$ (c=1, dichloromethane).

Melting point: 150° C. (methanol)(literature: 151° C., see Hungarian Patent Specification No. 163,769).

IR spectrum (KBr): 1700 cm$^{-1}$ (lactam).

The optical purity was determined on (−)-1α-ethyl-1β-methoxycarbonylethyl-1,2,3,4,6,7,12,12bα-octahydroindolo(2,3,a)quinolizine prepared by opening the lactame ring of (+)-14-oxo-E-homo-eburnane(3α,17α) as described below:

50 mg. of (+)-14-oxo-E-homo-eburnane(3α,17α) in a solution of 25 mg. of potassium tert.-butylate in 1 ml. of methanol are allowed to stand at room temperature for 2 to 3 hours. The progress of the reaction is monitored by thin layer chromatography. (The $R_f$-value of the starting compound is higher than that of the product obtained by opening the ring; KG-G, a 14:3 mixture of benzene and methanol.)

The reaction mixture is treated with 1 to 2 drops of acetic acid under cooling with ice and the solvent is eliminated in vacuo. The residue is dissolved in 2 ml. of dichloromethane, the pH of the solution is adjusted to 9 with 1 ml. of a 5% aqueous sodium carbonate solution, the organic phase is separated and the extraction is repeated with a further 2-ml. portion of dichloromethane. The organic phases are combined, dried on anhydrous magnesium sulfate, filtered and the solvent is distilled off from the filtrate in vacuo. As a distillation residue 58 mg. of (−)-1α-ethyl-1β-methoxycarbonylethyl-1,2,3,4,6,7,12,12bα-oxtahydro-indolo(2,3-a)quinolizine are obtained as an oily substance. $[\alpha]_D^{22} = -116°$, $[\alpha]_{546}^{22} = -40°$ (c=1.16, dichloromethane).

Optical purity:

$(-116°/-121°) = 0.96 = 96\%$

The chromatographically isolated product having a higher $R_f$-value weights 41 mg. (14.1%) and is identified as (+)-1α-14-oxo-3-epi-E-homo-eburnane.

The optical rotatory power of the crude oil is as follows: $[\alpha]_D^{22} = +107°$; $[\alpha]_{546}^{22} = +128°$ (c=1.0, dichloromethane).

The oily product, weighing 41 mg. is crystallized from 0.3 ml. of methanol to yield 31 mg. of crystalline (+)-14-oxo-3-epi-E-homo-eburnane, melting at 110° to 112° C. (ethanol). (The melting pont of this product according to the Hungarian Patent Application No. 781/80 amounts to 121° to 122° C. (isopropanol).

The IR, MS and NMR data of the compound are identical with the characteristics of the corresponding racemic compound (see Hungarian Patent Application RI-634).

EXAMPLE 6

(+)-14-Oxo-E-homo-eburnane(3α,17α)

100 mg. (0.307 mmoles) of (−)-1α-ethyl-1β-(hydroxycarbonyl-ethyl)-1,2,3,4,6,7,12,12bα-octahydro-indolo(2,3-a)quinolizine prepared according to the British Patent Specification No. 1,548,671 in 1 ml. of phosphorus oxychloride are allowed to stand at room temperature for 2 days. 3 ml. of benzene are added to the reaction mixture, whereupon the unreacted phosphorus oxychloride and benzene are distilled off in vacuo.

To the distillation residue 1 ml. of water is added and the pH is adjusted to 9 with a concentrated aqueous ammonium hydroxide solution, under cooling with ice. The precipitated organic substance is extracted with three 2-ml. portions of dichoromethane, the organic phases are combined, dried on anhydrous magnesium sulfate, filtered and from the filtrate the solvent is distilled off in vacuo.

92 mg. of an oily distillation residue are obtained, which are crystallized from 1 ml. of ether to yield 76 mg. of the named compound. Yield: 80.0%. Melting point: 154° to 155° C. (ether).

IR spectrum (KBr): 1700 cm$^{-1}$ (lactam).

$[\alpha]_D^{23} = +19°$; $[\alpha]_{546}^{23} = +22°$ (c=1, dichloromethane).

The optical purity is determined on (−)-1α-ethyl-1β-methoxycarbonylethyl-1,2,3,4,6,7,12,12bα-octahydro-indolo(2,3-a)quinolizine prepared by opening the lactame ring of (+)-14-oxo-E-homo-eburnane(3α,17α), as described in Example 5.

The optical rotatory power of (−)-1α-ethyl-1β-methoxycarbonylethyl-1,2,3,4,6,7,12,12bα-octahydro-indolo(2,3-a)quinolizine is:

$[\alpha]_D^{23} = -118°$; $[\alpha]_{546}^{23} = -141°$ (c=1.06, dichloromethane) Optical purity:

(−118°/−121°)=0.98=98%.

The MS and NMR spectra of the compound as well as its physical and chemical properties are identical with the corresponding properties of the substance disclosed in the Hungarian Patent Specification No. 163 769.

We claim:

1. A process for an enantioselective synthesis of an optically active 14-oxo-E-homo-eburnane compound of the formula (Ia)

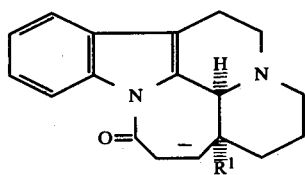

wherein R$^1$ is alkyl having from 1 to 4 carbon atoms, which comprises reacting an optically active 6-alkoxycarbonyl-hexahydroindoloquinolizinium salt of the formula (II)

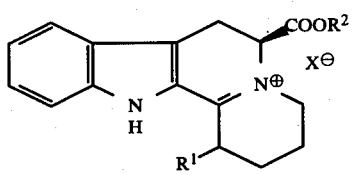

wherein
R$^2$ is alkyl having from 1 to 4 carbon atoms,
X is perchlorate, with a methylenemalonic acid diester derivative of the formula (III)

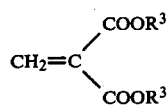

wherein R$^3$ is alkyl having from 1 to 4 carbon atoms, in the presence of a basic catalyst, subjecting the resulting optically active 6-alkoxycarbonyl-hexahydroindoloquinolizinium-1-yl-methylene malonate of the formula (IV)

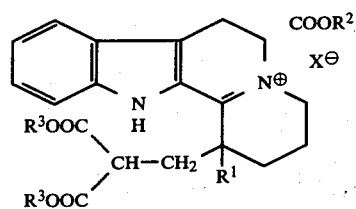

to acid and a subsequent alkaline hydrolysis, then subjecting the resulting active hexahydroindoloquiziniumdicarboxylic acid compound of the formula (V)

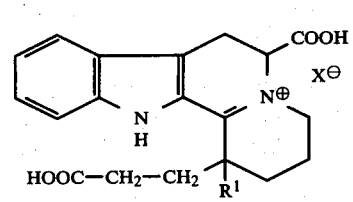

to selective decarboxylation, saturating the resulting optically active hexahydroindoloquinoliziniummonocarboxylic acid of the formula (VI),

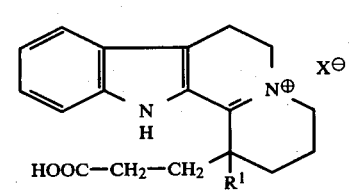

and cyclizing the resulting optically active octahydroindoloquinolizinemonocarboxylic acid of the formula (VII)

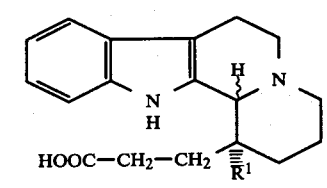

with or without isolation, or subjecting it to esterification after isolation, or esterifying an optically active hexahydroindoloquinoliziniummonocarboxylic acid of the formula (VI) and then saturating same, and finally subjecting a compound of the formula (VIII)

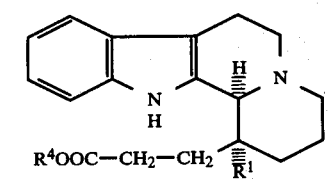

wherein R$^4$ is alkyl having from 1 to 4 carbon atoms, obtained by esterification and a subsequent saturation or saturation and a subsequent esterification, to ring closure.

2. The process defined in claim 1, in which an optically active 6-alkoxycarbonyl-hexahydroindoloquinolizinium salt of the formula (II) is reacted with a methylenemalonic acid diester derivative of the formula (III) in the presence of an alkali metal tert.-alcoholate as a basic catalyst.

3. The process defined in claim 2, in which 3 to 7 mol.%, preferably 4 to 6 mol.% of the basic catalyst are used calculated for the amount of the 6-alkoxycarbonyl-hexahydroindoloquinolizinium salt of the formula (II).

4. The process defined in claim 1 in which a methylenemalonic acid diester derivative of the formula (II) is employed in a molar excess of 1.1 to 2 over a 6-alkoxycarbonyl-hexahydroindoloquinolizinium salt of the formula (II).

5. The process defined in claim 1 wherein reactions are carried out in an organic solvent inert under the reaction conditions, said solvent being an aliphatic or aromatic hydrocarbon which can be substituted by one or more halogens.

6. The process defined in claim 1 which comprises carrying out the reactions at a temperature between 0° C. and 35° C., 7. The process defined in claim 1, in which the acid hydrolysis of the optically active 6-alkoxycarbonylhexahydroindoloquinolizinium-1-yl-methylenemalonate salt of the formula (IV) is performed with a mineral acid, easily removable when evaporating the reaction mixture.

8. The process defined in claim 1 which comprises carrying out the acid hydrolysis at a temperature between 80° C. and 120° C.

9. The process defined in claim 1, in which the alkaline hydrolysis subsequent to an acid hydrolysis of the optically active 6-alkoxycarbonyl-hexahydroindoloquinolizinium-1-yl-methylene malonate of the formula (IV) is carried out with an aqueous solution of an alkali metal hydroxide, in the presence of an alkanol having from 1 to 4 carbon atoms, as a co-solvent.

10. The process defined in claim 10 wherein the latter reaction is carried out at a temperature between 10° C. and 35° C.

11. The process defined in claim 1 in which the selective decarboxylation of the optically active hexahydroindoloquinoliziniumcarboxylic acid of the formula (V) is performed thermically at a temperature between 150° C. and 200° C.

12. The process defined in claim 11 in which the selective decarboxylation is carried out in an inert organic solvent, having a boiling point between 150° C. and 200° C.

13. The process defined in claim 1 in which the saturation of the optically active hexahydroindoloquinoliziniummonocarboxylic acid of the formula (VI), is performed with catalytically activated hydrogen.

14. The process defined in claim 13 in which saturation is carried out by hydrogenation in the presence of a palladium-on-charcoal catalyst in a solvent, inert under the reaction conditions.

15. The process defined in claim 13 in which dimethyl formamide is used as an inert solvent for the hydrogenation.

16. The process defined in claim 1 in which the cyclization of the optically active octahydroindoloquinoliziniummonocarboxylic acid of the formula (VII) is carried out with a phosphorus oxyhalide.

17. The process of derfined in claim 16 in which cyclization is performed at a temperature between 10° C. and 100° C.

18. The process defined in claim 1 for the preparation of optically active 14-oxo-E-homo-eburnane compounds of the formula (Ia), which comprises subjecting the optically active hexahydroindoloquinolizinium-monocarboxylic acid of the formula (VI) to catalytic hydrogenation in the presence of a palladium-on-charcoal catalyst in dimethyl formamide, and subsequently cyclizing the resulting optically active octahydroindoloquinolizinemonocarboxylic acid of the formula (VII) without isolation from the reaction mixture, with phosphorus oxychloride, at a temperature between 10° C. and 100° C.

19. The process defined in claim 1 in which the esterification of the optically active octahydroindoloquinolizinemonocarboxylic acid of the formula (VII) is carried out with diazomethane.

20. An optically active 6-alkoxycarbonyl-hexahydroindoloquinolizinium-1-yl-methylenemalonate of the formula (IV)

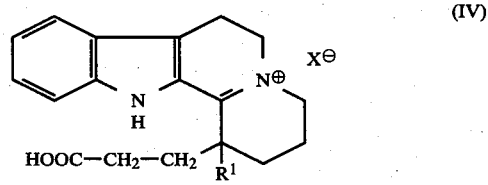

(IV)

wherein $R^1$, $R^2$ and $R^3$ indpendently represent alkyl having from 1 to 4 carbon atoms and X stands for perchlorate.

21. (−)-1α-Ethyl-1β-(2′,2′-diethoxycarbonylethyl)-6β-methoxycarbonyl-1,2,3,4,6,7-hexahydro-12H-indolo(2,3-a)-quinolinium-5-ium perchlorate as defined in claim 20.

22. An optically active hexahydroindoloquinolizinium-dicarboxylic acid of the formula (V),

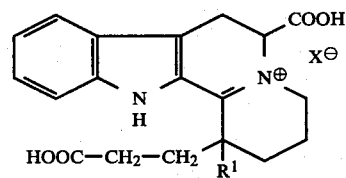

wherein $R^1$ is alkyl having from 1 to 4 carbon atoms and X stands for perchlorate.

23. (+)-1α-Ethyl-1β-carboxyethyl-6-carboxy-1,2,3,4,6,7-hexahydro-12H-indolo(2,3-a)quinolizin-5-ium perchlorate as defined in claim 22.

24. An optically active hexahydroindoloquinoliziniummonocarboxylic acid of the formula (VI)

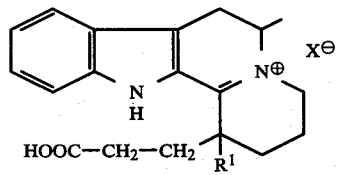

wherein $R^1$ is alkyl having from 1 to 4 carbon atoms and X stands for perchlorate.

25. (−)-1α-Ethyl-1β-carboxyethyl-1,2,3,4,6,7-hexahydro-12H-indolo(2,3-a)quinolizin-5-ium perchlorate as defined in claim 24.

* * * * *